United States Patent [19]

Bonutti

[11] Patent Number: 5,213,094

[45] Date of Patent: May 25, 1993

[54] ORTHOSIS WITH JOINT DISTRACTION

[76] Inventor: Peter M. Bonutti, 1303 W. Evergreen Plz., Effingham, Ill. 62401

[21] Appl. No.: 686,811

[22] Filed: Apr. 17, 1991

Related U.S. Application Data

[63] Continuation-in-part of Ser. No. 559,700, Jul. 30, 1990, Pat. No. 5,167,612.

[51] Int. Cl.$^5$ ............................................... A61F 5/00
[52] U.S. Cl. .................................... 128/25 R; 602/16
[58] Field of Search ................... 602/5, 16, 20, 23, 26; 482/124, 130, 139; 128/25 R, 25 B, 26, 25 C

[56] References Cited

U.S. PATENT DOCUMENTS

| | | |
|---|---|---|
| 3,814,419 | 6/1974 | Bjorklund et al. . |
| 3,976,057 | 8/1976 | Barclay ............... 128/25 R |
| 4,039,183 | 8/1977 | Sakurada . |
| 4,180,870 | 1/1980 | Radulovic et al. . |
| 4,214,577 | 7/1980 | Hoy ..................... 128/25 R |
| 4,237,873 | 12/1980 | Terry et al. . |
| 4,441,489 | 4/1984 | Evans et al. . |
| 4,456,002 | 6/1984 | Barber et al. . |
| 4,502,681 | 3/1985 | Blomqvist ............ 482/130 |
| 4,508,111 | 4/1985 | Hepburn . |
| 4,538,595 | 9/1985 | Hajianpour . |
| 4,538,600 | 9/1985 | Hepburn . |
| 4,606,542 | 8/1986 | Segal .................... 482/124 |
| 4,612,919 | 9/1986 | Best . |
| 4,665,905 | 5/1987 | Brown . |
| 4,718,665 | 1/1988 | Airy et al. ........... 482/139 X |
| 4,790,301 | 12/1988 | Silfverskiold . |
| 4,844,454 | 7/1989 | Rogers . |
| 4,848,326 | 7/1989 | Lonardo . |
| 4,930,497 | 6/1990 | Saringer . |
| 4,955,369 | 9/1990 | Bledsoe et al. . |
| 5,036,837 | 8/1991 | Mitchell et al. ....... 602/20 X |
| 5,102,411 | 4/1992 | Hotchkiss et al. ..... 128/25 R X |

FOREIGN PATENT DOCUMENTS

| | | |
|---|---|---|
| 0181688 | 9/1985 | European Pat. Off. . |
| 2829562 | 1/1980 | Fed. Rep. of Germany . |
| 8806231 | 5/1988 | Fed. Rep. of Germany . |
| 8804543 | 12/1986 | PCT Int'l Appl. . |
| 1426580 | 9/1988 | U.S.S.R. . |

OTHER PUBLICATIONS

Singer European Patent Application No. 0 380 060, filed Jan. 23, 1990.
Practitioner Information for Dynasplint LPS Orthosis—Knee Extension by Dynasplint Systems, Inc.

Primary Examiner—Richard J. Apley
Assistant Examiner—Linda C. M. Dvorak
Attorney, Agent, or Firm—Tarolli, Sundheim & Covell

[57] ABSTRACT

An orthosis for extension and flexion of a joint of a limb provides for distraction of the joint upon extension. In one embodiment, a spreading arrangement positively moves the orthosis arms longitudinally outwardly relative to each other upon rotation from a flexed position to an extended position. In another embodiment, the axis of rotation of the orthosis arms is located outwardly from the axis of rotation of the limb. Upon rotation of the arms relative to each other from a flexed position to an extended position, the orthosis arms move longitudinally outwardly because of the geometry of the orthosis. Because the cuffs on the arms are clamped to the limb segments, the limb segments are also forced outwardly, providing joint distraction. Structure is provided for limiting the amount of joint distraction and avoiding injury to the joint. The inner ends of the orthosis arms are linked together to maintain them in position relative to each other. The cuffs which attach the arms to the limb segments are adjustable longitudinally along the arms, to provide for different positions of the cuffs on the on limb, different length limbs, and the use of the orthosis on either a knee joint or an elbow joint.

30 Claims, 7 Drawing Sheets

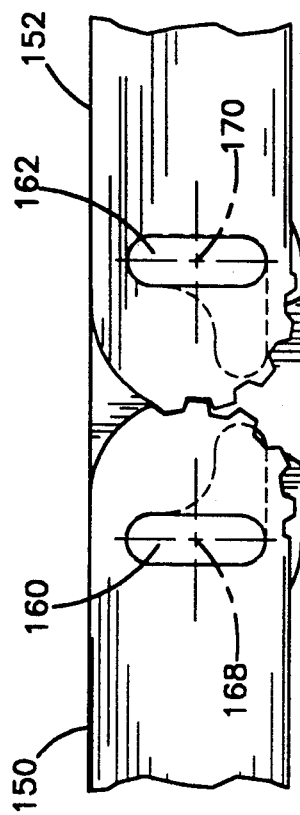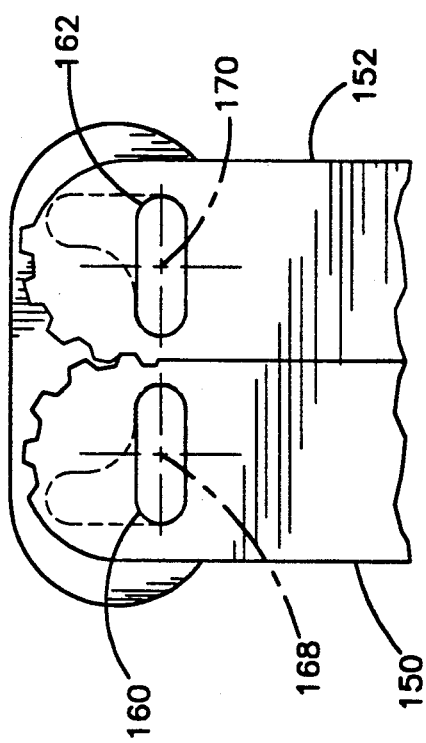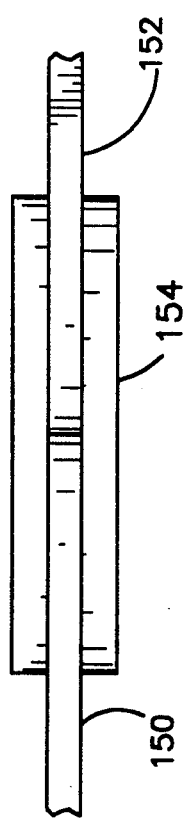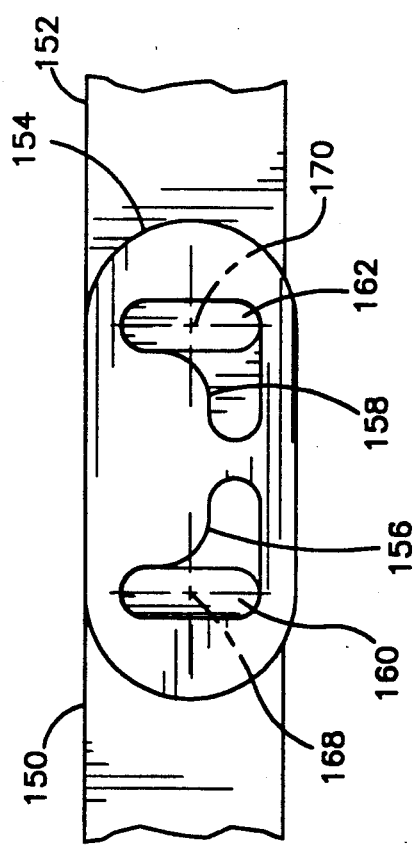

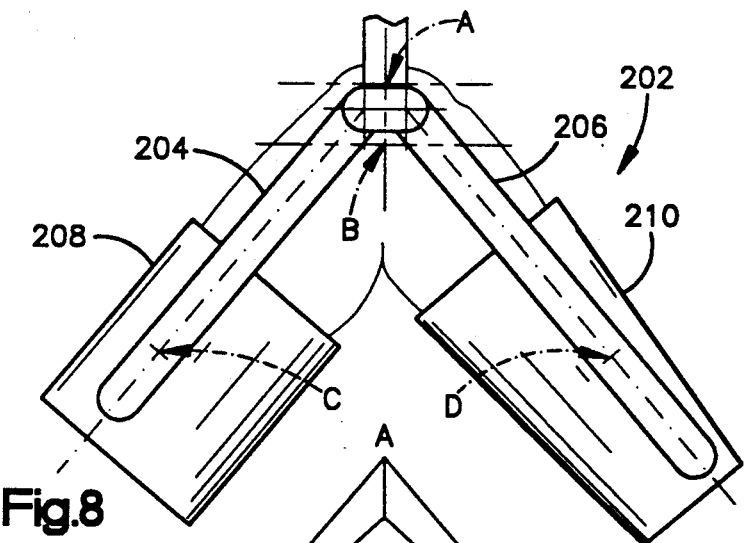
Fig.8
Fig.8A
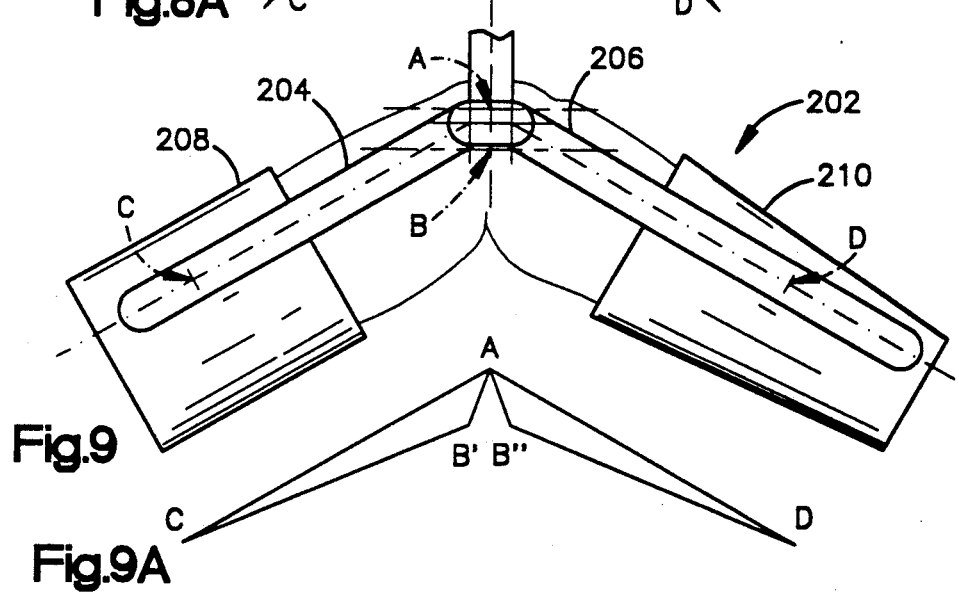
Fig.9
Fig.9A
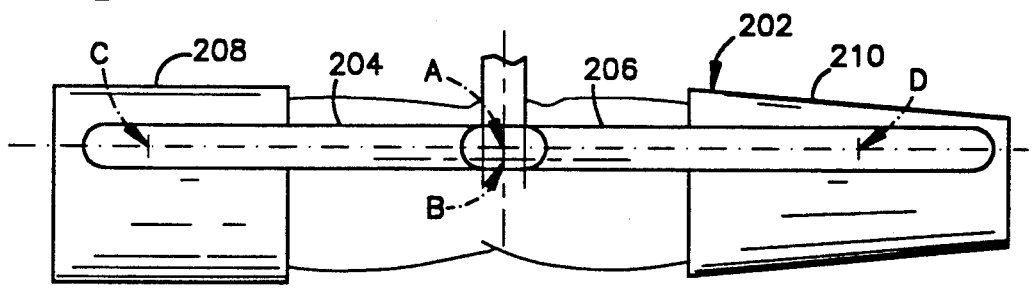
Fig.10
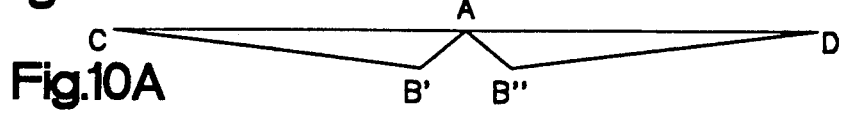
Fig.10A

ORTHOSIS WITH JOINT DISTRACTION

RELATED APPLICATION

This application is a continuation-in-part of my co-pending application Ser. No. 559,700, filed Jul. 30, 1990, entitled Adjustable Orthosis, now U.S. Pat. No. 5,167,612. This application claims the benefit of the filing date of said application for all common subject matter.

BACKGROUND OF THE INVENTION

1. Technical Field

The present invention relates to an adjustable orthosis for stretching tissue in the human body. In particular, the present invention relates to an adjustable orthosis which distracts a joint during extension of the joint.

2. Description of the Prior Art

In circumstances in which full extension of a joint in a human limb is not available, such as after surgery or trauma, the joint stiffens and loses its full range of motion. Various devices have been designed to flex and extend the joint to regain range of motion.

U.S. Pat. No. 4,612,919 shows an adjustable limb support for adjustably orienting the forearm and upper arm of a human patient in a variety of angular relationship to therapeutically treat the contracted muscles in the patient's arm.

U.S. Pat. No. 4,848,326 shows a knee contracture correction device for straightening a contracted knee.

U.S. Pat. No. 4,538,600 shows an adjustable splint assembly with a lower strut and an upper strut pivotably connected to the lower strut. An internal spring applies a force at the pivot point to align the upper and lower struts to straighten the limb to which the splint is attached. A similar device is also shown in U.S. Pat. No. 4,508,111. Similar devices are in use and are sold under the trademark DYNASPLINT by Dynasplint Systems, Inc.

U.S. Pat. No. 4,665,905 shows a dynamic elbow and knee extension device with a centrally positioned compression spring.

It is also known in the art to put a rigid element including a turnbuckle, on the inside angle of a joint, between two cuffs attached to limb segments and use the turnbuckle to vary the length of the rigid element to pull and push the limb segments relative to each other. It has been found that this device does not work very well in practice because it is cumbersome and difficult to obtain relatively full extension or flexion at the extremes of motion.

When the joint stiffens, joint tissues such as ligaments, tendons, and muscles around the bones also become compressed and less flexible. Therefore, joint therapy should not merely seek to improve the range of motion of the joint (that is, the angle through which the joint can be flexed and extended). Rather, joint therapy should be also directed to obtaining distraction of the joint. "Distraction" is defined by one dictionary as "Separation of the surfaces of a joint by extension without injury or dislocation of the parts." (*Taber's Cyclopedic Medical Dictionary*, 16th Edition, 1989, page 521), and involves stretching the joint capsule, soft tissue, ligaments, and tendons. Further, it is also desirable to distract the joint without increasing the joint reactive force.

None of the above-identified prior art devices, and none of the devices in use at the present time, functions to distract the joint upon extension of the joint. None allows the patient to provide the needed therapy by himself, without the assistance of a therapist who manually stretches the joint. None allows the patient to control the therapy process in a self-directed manner. Accordingly, it is desirable to provide a device which not only enhances the range of motion of the joint but also distracts the joint and stretches soft tissue.

SUMMARY OF THE INVENTION

In my earlier filed co-pending application identified above, I disclosed an adjustable orthosis having certain novel features and advantages. The present invention is an improved version of the earlier orthosis.

Like the earlier orthosis, the orthosis of the present invention can be set up for both extension and flexion of a joint. The tower mechanism is also retained to provide mechanical advantage for increasing the range of motion of the joint. Furthermore, all the advantages of the use of the flexible member as a force-transmitting means are retained, including the ease of obtaining incremental adjustment of the orthosis.

In the present invention, the inner ends of the orthosis arms are linked together to maintain them in position relative to each other. Also, the cuffs which attach the arms to the limb segments are adjustable longitudinally along the arms, to provide for different positions of the cuffs on the limb, different length limbs, and the use of the orthosis on either a knee joint or an elbow joint.

The present orthosis is specifically operable to distract the joint which is being extended. Joint distraction upon extension is desirable for the reasons set forth above. Further, it is desirable to distract the joint without increasing the joint reactive force.

Accordingly, in the present invention, the cuffs are designed to clamp securely enough on the limbs so that force may be applied in a longitudinally outward direction upon extension of the joint by the orthosis. This effectively pushes the limb segments apart and distracts the joint. To limit (control) the amount of joint distraction and avoid injury to the joint, the cuffs can be spring loaded for safety, and slide longitudinally inwardly along the arms upon the generation of distraction force in excess of a predetermined amount. The amount of distraction force applied to the joint can also be controlled with the use of a slip clutch in the ratchet, by putting an elastic portion in the cable, or by putting a weakened portion in the cable.

In the present invention there are disclosed several structures for providing the distraction force.

One structure is a "spreading arrangement" which positively moves the orthosis arms longitudinally outwardly relative to each other upon rotation from a flexed position to an extended position. For example, a pin and cam slot arrangement can be used to spread apart the inner ends of the orthosis arms. Another "spreading arrangement" employs asymmetrical or eccentric arm ends which are geared together. Upon rotation of the orthosis arms relative to each other from a flexed position to an extended position, the asymmetrically shaped arm ends force the arms longitudinally outwardly. In either case, because the cuffs on the arms are clamped to the limb segments, the limb segments are also forced outwardly, providing joint distraction.

Another structure for providing distraction force locates the axis of rotation of the orthosis arms outwardly from the axis of rotation of the limb. Upon rotation of the arms relative to each other from a flexed position to an extended position, the limb segments, besides pivoting, are also moved longitudinally outwardly because of the geometry of the orthosis and its attachment position relative to the limb. If this orthosis geometry is used, a spreading arrangement is not necessary, although it may also be used.

In the present invention, the drive means for moving the orthosis arms is preferably a ratchet located on one of the cuffs rather than on the tower, although the ratchet can be located anywhere along the length of the flexible member. Further, drive means other than a ratchet are disclosed in the present invention. Also, the orthosis can be used on other joints with appropriate modifications to structure, and several different such modifications are disclosed herein.

The present invention provides the first system available for a therapy patient which the patient can operate himself and which will provide the amount of force necessary to re-establish the terminal extremes of motion in a joint. No prior device provided the amount of force necessary to re-establish the terminal extremes of motion in a joint. The mechanical advantage provided by the present system, in conjunction with the light weight and portability of the device, mean that the patient can reduce or eliminate the need for a therapist to manually stretch the joint. This will also decrease the time needed in the hospital, as the patient can easily operate the orthosis of the present invention, at home, in a safe and effective manner.

BRIEF DESCRIPTION OF THE DRAWINGS

The foregoing and other features of the present invention will become apparent to one skilled in the art upon a consideration of the following description of the invention with reference to the accompanying drawings, wherein:

FIGS. 5, 5A, 5B and 5C are series of enlarged views of portions of the orthosis of FIG. 4;

FIGS. 8 and 8A are schematic views of an orthosis having its axis of rotation outward of the joint axis of rotation to effect joint distraction upon extension;

FIGS. 9 and 9A are views similar to FIG. 8, with the orthosis in a more extended position;

FIGS. 10 and 10A are views similar to FIG. 8 with the orthosis in an even more extended position;

DESCRIPTION OF PREFERRED EMBODIMENT

Figure 1:
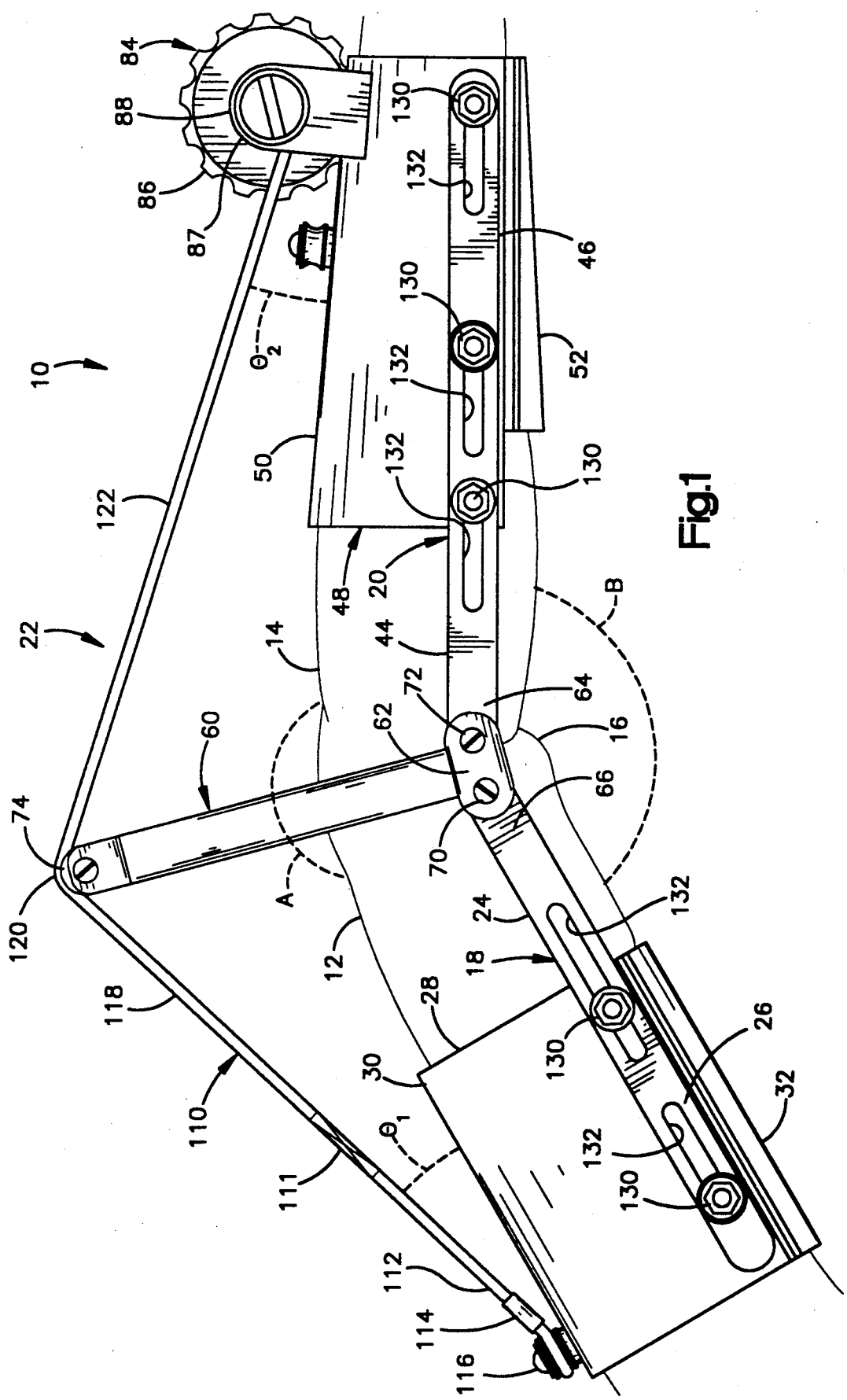
FIG. 1 is a view of an orthosis in accordance with the present invention.

FIG. 1 illustrates an orthosis 10 in accordance with the present invention on a human limb including an upper arm 12 and a forearm 14 pivotally connected at an elbow joint 16. The orthosis 10 is illustrated as set up to extend (straighten) the elbow joint 16, although it should be understood that the orthosis 10 can also be set up to flex (bend) the elbow joint 16, as will be described later. It should also be understood that the orthosis 10 can be used to extend or flex other joints in the body, such as a knee, wrist, finger, or ankle joint, with the construction and dimensions of the orthosis 10 in such case being suitable varied to fit the particular application. The orthosis can be used, for example, to flex the ankle joint to stretch a tight achilles tendon. It is especially useful in obtaining the last degrees of joint extension. The orthosis can be custom made to fit a particular individual, or can be an off the shelf item. The orthosis can also be used, for example, to eliminate contractures or stress soft tissue. It can be used for patients with cerebral palsy, stroke, spastic paralysis, as well as in post-traumatic or post-surgical cases. It can also be used, for example, to establish terminal motion in therapy after joint surgery such as a knee replacement, in which the extremes of motion are difficult to obtain without extensive intervention of a therapist.

The orthosis 10 includes a first arm assembly 18, a second arm assembly 20, and an actuator assembly 22 operable to pivot the first arm assembly 18 relative to the second arm assembly 20 to move the joint 16. (As used herein, to "move" a joint means either to extend the joint or to flex the joint.)

The first arm assembly 18 includes a rigid longitudinally extending arm 24. To the outer end portion 26 of the arm 24 is attached a first cuff assembly 28. The first cuff assembly 28 includes a rigid cuff portion 30 and a flexible cuff portion 32. The rigid cuff portion 30 extends approximately halfway circumferentially about the upper arm 12, and the flexible cuff portion 32 wraps about the remainder of the upper arm 12. Suitable fastening means which may be, for example, Velcro ® fastener or orthoplast is used to secure the first cuff assembly 28 to the upper arm 12 so that the first arm assembly 18 may apply torque to the upper arm 12.

The first arm assembly 18 also includes a second rigid longitudinally extending arm, which is not shown because it is behind the upper arm 12. An outer end portion of the second arm is also attached to the rigid cuff portion 30 of the first cuff assembly 28. The second arm extends parallel to the arm 24 and is spaced apart from the arm 24, with the arm 24 and the second arm on opposite sides of the upper arm 12 of the limb.

The second arm assembly 20 includes a rigid longitudinally extending arm 44. To an outer end portion 46 of the arm 44 is attached a second cuff assembly 48. The second cuff assembly includes a rigid cuff portion 50 and a flexible cuff portion 52 attached thereto. The rigid cuff portion 50 extends approximately halfway about the forearm 14, and the flexible cuff portion 52 wraps about the remainder of the forearm 14. Suitable fastening means such as Velcro ® fastener is used to secure the second cuff assembly 48 about the forearm 14, so that the second arm assembly 20 can apply torque to the forearm 14.

The second first arm assembly 20 also includes a fourth rigid longitudinally extending arm, which is not shown because it is behind the forearm 14. An outer end portion of the second arm is also attached to the rigid cuff portion 50 of the second cuff assembly 48. The fourth arm extends parallel to the arm 44 and is spaced apart from the arm 44, with the arm 44 and the fourth arm on opposite sides of the forearm 14 of the limb.

The actuator assembly 22 includes a tower 60 which provides a mechanical advantage for the orthosis 10 as described below. The tower can be any structure which performs this function, and need not be the particular structure shown herein. The tower 60 has a tower connecting portion 62 to which the inner end portions 64 and 66 of the arms 44 and 24 respectively are connected. The tower connecting portion 62 secures the arm 24 for pivotal movement about a pivot point 70, and the arm 44 for pivotal movement about a pivot 72. The tower 60 includes a similar structure to connect the second and fourth arms (not shown) on the back of the limb.

The tower 60 supports a pulley 74 at a substantial distance from the pivot points 70 and 72 of the arms 24 and 44, and at a distance from the pivot points of the second and fourth arms (not shown). The tower 60 preferably supports the pulley 74 at a substantial distance from the pivot points 70 and 72 of the arms 24 and 44, and at a substantial distance from the pivot points of the second and fourth arms (not shown). By "substantial" is meant far enough to provide a mechanical advantage as compared to orthoses which apply force at a location adjacent the axis of rotation of the joint. The benefit of this is discussed later herein. The upper arm 12, elbow joint 16, and forearm 14 define on one side of the joint 16 an inner sector "B" (inside the bend of the limb) which decreases in angle as the joint 16 is flexed. The upper arm 12, the elbow joint 16, and the forearm 14 define on the opposite side of the joint 16 an outer sector "A" which decreases in angle as the joint 16 is extended (straightened). The tower 60 and the pulley 74 are located in the outer sector "A".

A winch 84 is mounted on the second cuff assembly 48. The winch 84 includes a knob 86 and a ratchet drive assembly 88. The winch 84 may be of a known ratchet-type construction operable to repeatedly and successively wind a flexible member in one direction without allowing it to be unwound.

A flexible member 110 is included in the actuator assembly 22. In the preferred embodiments, the flexible member 110 is a cable. It could also be a rope or a urethane belt, for example. A first end portion 112 of the cable 110 terminates in a clip 114 which is fixed via a pin 116 to the rigid cuff portion 30 of the first arm assembly 18. A portion 118 of the cable extends from the clip 114 to the pulley 74. A portion 120 of the cable 110 wraps around the pulley 74. A portion 122 of the cable extends from the pulley 74 to the winch 84. The cable 110 is windable by the winch 184 in a known manner. Thus, both ends of the cable 110 are fixed to the cuff assemblies, and the cable 110 is windable by the winch 84.

In accordance with one feature of the present invention, the cuff assemblies 28 and 48 may be adjustable for position longitudinally along the arm assemblies 18 and 20, respectively. Each cuff assembly includes two bolts or mounting members 130 fixed to the rigid cuff portion and received in slots 132 in the orthosis arm. The mounting members 130 may be loosened to permit the cuff assemblies to be slid to another position along the arm, then tightened to lock it in place. Thus, the orthosis may be used on different length limbs, on a leg rather than an arm, or to apply force to the limb at a different location.

Figure 7:
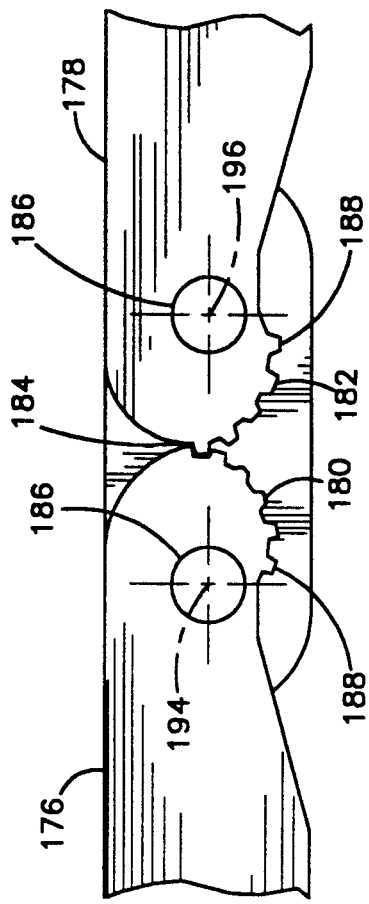
FIGS. 7, 7A, 7B and 7C are a series of enlarged views of portions of the orthosis of FIG. 6.

In accordance with a further feature of the present invention, the longitudinally inner ends of the arms 24 and 44 are linked together for movement together. As seen in FIGS. 5 and 7, the inner end of each arm assembly has a plurality of gear teeth which engage a corresponding set of gear teeth on the other arm. Thus, as one arm pivots, the other arm pivots in the opposite direction. This structure also ensures that the tower 82 also remains in position to apply force to the arm assemblies. Other methods of linking the arms may be used.

The orthosis 10 is operated to extend a joint such as the joint 16 in the following manner. The first cuff assembly 28 is fastened or clamped to the upper arm 12 tightly enough so that the first arm assembly 18 may apply torque to the upper arm 12 without having the cuff assembly 28 slide along the upper arm 12. Similarly, the second cuff assembly 48 is fastened or clamped to the forearm 14 so that the second arm assembly 20 may apply torque to the forearm 14 without the cuff assembly 48 sliding along the forearm 14. The ratchet drive assembly 88 of the winch 84 is then rotated to wind the cable 110. The cable 110 is partially wound onto the winch 84. Because the cable end 112 is fixed to the first cuff assembly 28, and the winch 84 is fixed to the second cuff assembly 48, the cuff assemblies 28 and 48 are drawn toward the pulley 74. The first arm assembly 18 pivots about the pivot point 70, and the second arm assembly 20 pivots about the pivot point 72. As the arm assemblies 18 and 20 pivot, the upper arm 12 and forearm 14, to which they are attached, also pivot. This moves or extends the joint 16 as desired.

An advantage of the ratchet drive mechanism is that it can be provide an automatic locking mechanism for blocking movement of the parts of the orthosis in an undesired direction. The ratchet drive mechanism 84 (FIG. 1) is operative to wind the cable 110 in one selected direction, while blocking unwinding movement of the cable 110 in the opposite direction. Thus, the patient can turn the knob 86 in the desired direction to wind the cable 110 in the desired direction and thereby move the joint to which the orthosis is attached from a first position to a second position, then release the knob 86. The ratchet mechanism holds the cable 110 from winding back in the opposite direction, thus holding the joint in the second position. Therefore, if force is applied to the orthosis to extend a joint slightly against the resistance of the soft tissues of the joint, then the force is released, the orthosis and joint will maintain that extended position, and will not revert to the starting position.

It is desirable to thus maintain a joint in a selected position, because tissue is viscoelastic. That is, tissue will stretch a certain amount, then if it is maintained in that stretched condition for a period of time, will be able to stretch even more. This is the best way to establish or reestablish a range of motion in the soft tissues around a joint, as it does not involve damaging the tissue.

Accordingly, with an orthosis in accordance with the present invention, a patient can apply force to stretch tissue a desired amount by moving the orthosis from a first position to a second position. The patient can then stop applying force to the orthosis. The orthosis remains in the second position. The patient allows the tissue to remain in the stretched condition. The patient can then apply force to stretch tissue a further desired amount by moving the orthosis from the second position to a third position. This repeated stretching and resting of the tissue properly reestablishes a range of motion in the joint.

As the orthosis 10 is adjusted to extend the joint 16 from a relatively flexed position to a relatively extended position, the acute angle $\Theta_1$ (FIG. 1) between the cable portion 118 and the first arm assembly 18 increases. At the same time, the acute angle $\Theta_2$ (FIG. 1) between the cable portion 122 and the second arm assembly 20 also increases as the orthosis 10 is adjusted from a relatively flexed position to a relatively extended position.

The torque applied by a cuff assembly to its respective limb portion is equal to (1) the force applied along the cable portion extending from the pulley 74 to that arm assembly, times (2) the length of the lever arm of that arm assembly, times (3) the sine of the angle between the cable portion and the arm assembly. For example, referring to FIG. 1, the torque applied to the first arm assembly 18 at the pin 116 is equal to the force applied along the cable portion 118, times the lever arm (which is equal to the distance between the pivot 70 and the pulley 74), times the sine of the angle $\Theta_1$ between the cable portion 118 and the arm 24.

As the orthosis 10 is adjusted from a relatively flexed position to a relatively extended position, the angle between a cable portion (118 or 122) and its respective arm assembly (18 or 20) increases. Thus, the sine of the angle between the cable portion and the arm assembly also increases. For any given orthosis, the length of the lever arm is a constant. Thus, assuming a constant force applied by the winch 84 pulling on the cable 110, an increasing amount of torque is applied by the arm assembly to the limb portion as the orthosis 10 is adjusted from a relatively flexed position to a relatively extended position.

Since terminal stretching is the most difficult to obtain in a human joint, the orthosis of the present invention is highly advantageous in that the amount of torque available to pivot the upper arm relative to the forearm increases as the joint is extended because of the mechanical advantage provided by the tower 60. The orthosis provides a large straightening force through the full range of motion because it maintains a significant vertical (extension) force vector through the full range of motion. Of course, this assumes a sufficient force applied to and by the winch 84, and is it understood that more force may be needed to turn the winch 84 as the joint is fully extended to overcome the stiffness of the joint.

The force vector representative of the pulling force extending along the flexible member 110 can be resolved into a component extending in a direction parallel to the arm assembly and a component extending in a direction perpendicular to the arm assembly. The force component extending in the direction perpendicular to the arm assembly is representative of the magnitude of the net extension force applied to the arm assembly to extend the joint. This component is equal to the sine of the angle between the flexible member and the arm assembly, times the force in the direction along the flexible member.

The net extension force is therefore directly proportional to the sine of the angle between the flexible member and the arm assembly. Thus, to increase the extension force applied to the arm assembly, the angle can be increased. It can be seen that one way to increase the angle is to increase the distance between the pivot point for the arm assembly and the pulley 74. Thus, it is evident that the longer the support member or tower, the greater the extension force. This is done by pivoting away from the actual axis of joint motion or applying force at a site removed from the joint axis of rotation.

Thus, the structure of the orthosis 10 is clearly advantageous as compared to, for example, a prior art device which applies its force at a location closely adjacent to the joint. For such a prior art device, the distance between the force application point and the pivot point of the arm is very short. Thus, the angle between (a) the arm and (b) a line extending between the cuff assembly and the force generation point, is always extremely small. Accordingly, the amount of torque which can be generated is extremely limited. Thus, having the force application point (in this case represented by the pulley 74) spaced at a substantial distance from the pivot points 70 and 72 by the tower 60, as in the illustrated embodiments, provides a substantial mechanical advantage.

It can also be seen that, when the winch 84 pulls on the flexible member 110, a reaction force is developed in the rigid tower or support member 60. The reaction force extends along the tower 60 in the direction from the pulley 74 to the pivots 70 and 72 and to the pivots for the second and fourth arms (not shown). The reaction force tends to push in one direction on the inner end portions of the orthosis arms 24 and 44 while the pulling force generated by the winch 84 moves the outer end portions of the same arms in the opposite directions. Thus, the actuator assembly 22 simultaneously applies oppositely directed forces to opposite ends of the arm assemblies 18 and 20 to provide an even more efficient pivoting motion to extend the joint 16.

Figure 2:
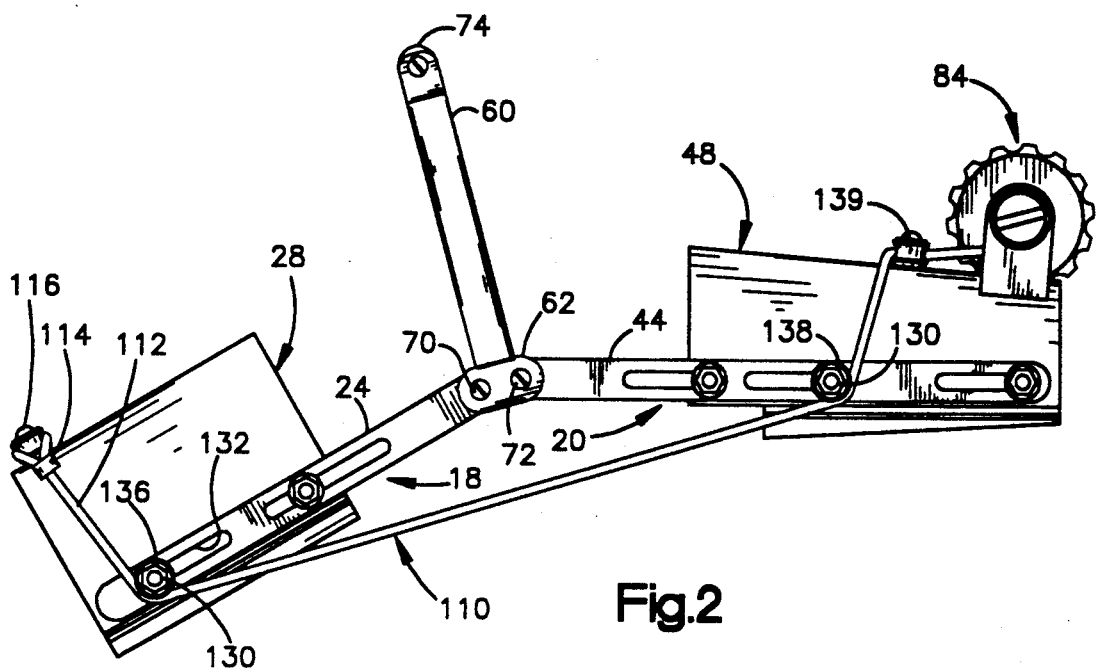
FIG. 2 is a view of the orthosis of FIG. 1 set up for flexion.

The orthosis 10 is illustrated in FIG. 1 as being used to extend or flex a joint. The orthosis 10 can also be used to flex a joint as illustrated in FIG. 2. This is done by rerouting the flexible member 110. The end portion 112 of the flexible member 110 remains fixed by the pin 116 to the first cuff assembly 28. The cable 110 extends underneath a pulley 136 fixed to the cuff assembly 28, to a pair of pulleys 138 and 139 fixed to the cuff assembly 48, the winch 84. When the winch 84 is then operated, the cable 110 is wound by the winch 84. The second cuff assembly 48 is drawn toward the first cuff assembly 28. Because the inner ends of the arm assemblies 18 and 20 are fixed to the tower 82 the arm assemblies 18 and 20 pivot relative to each other, decreasing the included angle between them. Since the arm assemblies 18 and 20 are fixed the limb portions 12 and 14, the joint 16 is flexed.

When the orthosis 10 is set up for flexion in this manner, no mechanical advantage is derived from the tower 38. However, all the advantages of the flexible member 110 are retained, including the ease of obtaining incremental motion.

It is to be noted that in FIGS. 1 and 2 the winch 84 is mounted on the cuff assembly 48. However, the winch 84, or whatever drive means is used to apply force to the flexible member 100, could be located at any feasible location along the length of the flexible member 110. Furthermore, it is to be noted that, with appropriate dimensional modifications, this design is suitable for use on joints of the body other than the knee and the elbow, such as the wrist, the ankle, and the fingers, and accordingly, the invention is not limited in that respect.

As noted above, it is desirable to distract the joint upon extension. Accordingly, since the cuff assemblies clamp on the upper arm 12 and the forearm 14, force may be applied in a longitudinally outward direction to push the limb segments apart. Structure for generating distraction force is described below. For safety, the amount of distraction must be limited to avoid injury to the joint.

Figure 3:
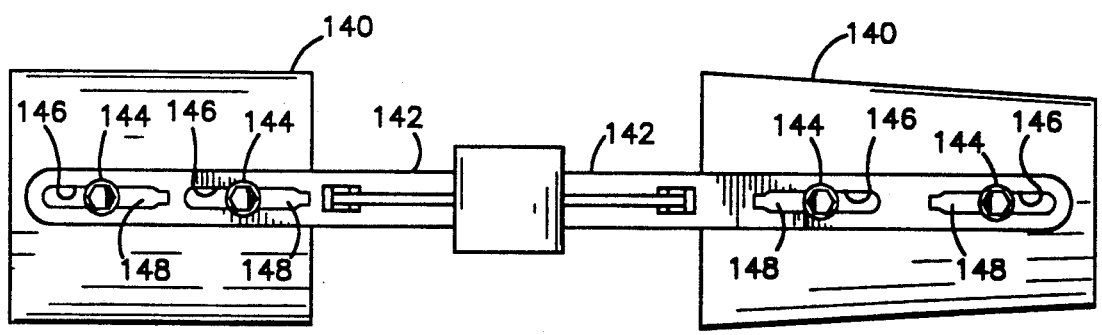
FIG. 3 is a top plan view of an orthosis having slidably mounted cuff assemblies.

Thus, the cuff assemblies (FIG. 3) of a representative orthosis according to the present invention are preferably spring loaded for safety and to maintain distraction. The cuff assembly 140 is slidably mounted to the arm 142 by a pair of mounting members 144 received in slots 146. A pair of springs 148 bias the mounting members 144 outwardly relative to the arm 142. Together, the two springs 148 exert a predetermined amount of force on the cuff assembly 140. If the amount of distraction force applied to the cuff assembly exceeds that amount, the springs 148 yield, allowing the cuff assembly 140 to slide longitudinally inwardly on the arm 142 and relieving the force on the joint being extended.

Alternative structures for limiting the amount of distraction force include the provision of a slip clutch which may be of a known construction in the ratchet drive assembly as indicated schematically at 87 (FIG. 1; the use of an elastic cable as the flexible member 110 which yields (elongates) upon exceeding a predetermined amount of stress; or the provision of a weakened or frangible portion in the cable which breaks upon exceeding a predetermined amount of stress, as indicated schematically at 111 (FIG. 1).

Next are described several structures for providing distraction force to move the arms of an orthosis longitudinally outwardly upon extension.

Figure 4:
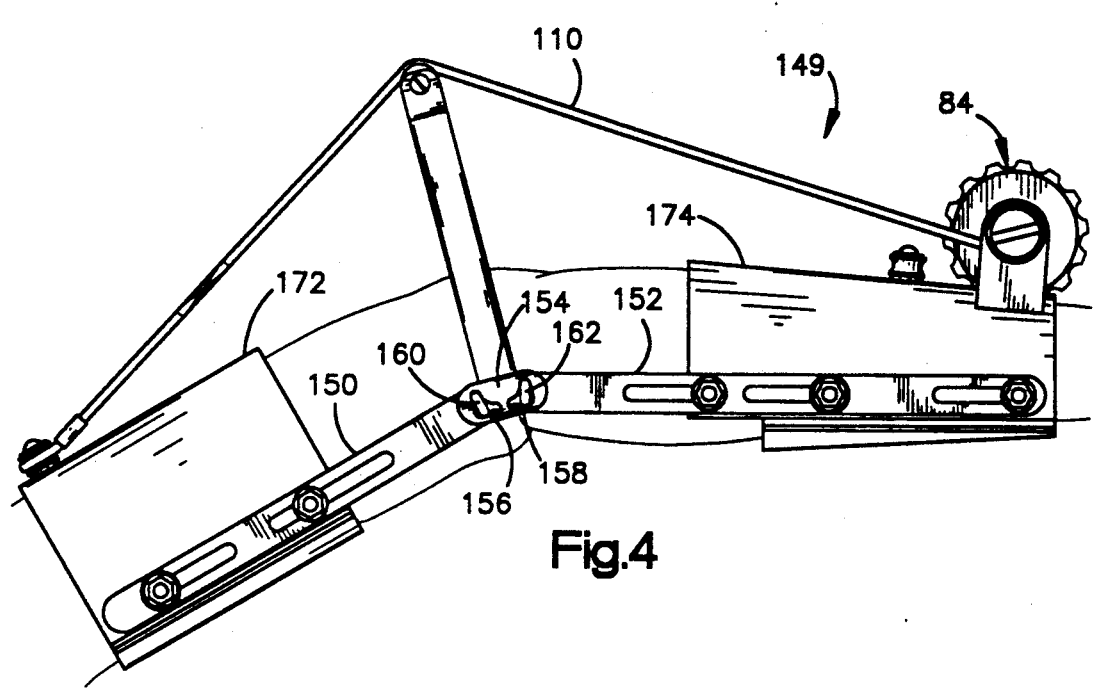
FIG. 4 is a view of an orthosis having a cam slot and pin arrangement to effect joint distraction upon extension.

The orthosis 149 illustrated in FIGS. 4–5 includes a pair of orthosis arms 150 and 152 interconnected by a connector 154. A pair of cam slots 156 and 158 are formed in the connector 154. A pin 160 on the arm 150 extends through the slot 156. A pin 162 on the arm 152 extends through the slot 158. A set of gear teeth 164 on the inner end of the arm 150 mesh with a set of gear teeth 166 on the inner end of the arm 152.

The cam slots 156 and 158 are configured so that, as the arms 150 and 152 move from a relatively flexed position as viewed in FIG. 5B to a relatively extended position as viewed in FIG. 5C, the cam slots force the pins 160 and 162 longitudinally outwardly relative to each other. This movement is evident from a comparison of the relative locations of the pin centers 168 and 170 in FIG. 5B with their relative locations in FIG. 5C. Thus, upon rotation of the orthosis arms 150 and 152 relative to each other from a flexed position to an extended position, the orthosis arms have moved longitudinally outwardly. Because the cuffs 172 and 174 on the orthosis arms are clamped to the limb segments, the limb segments are also forced outwardly, providing joint distraction.

Figure 6:
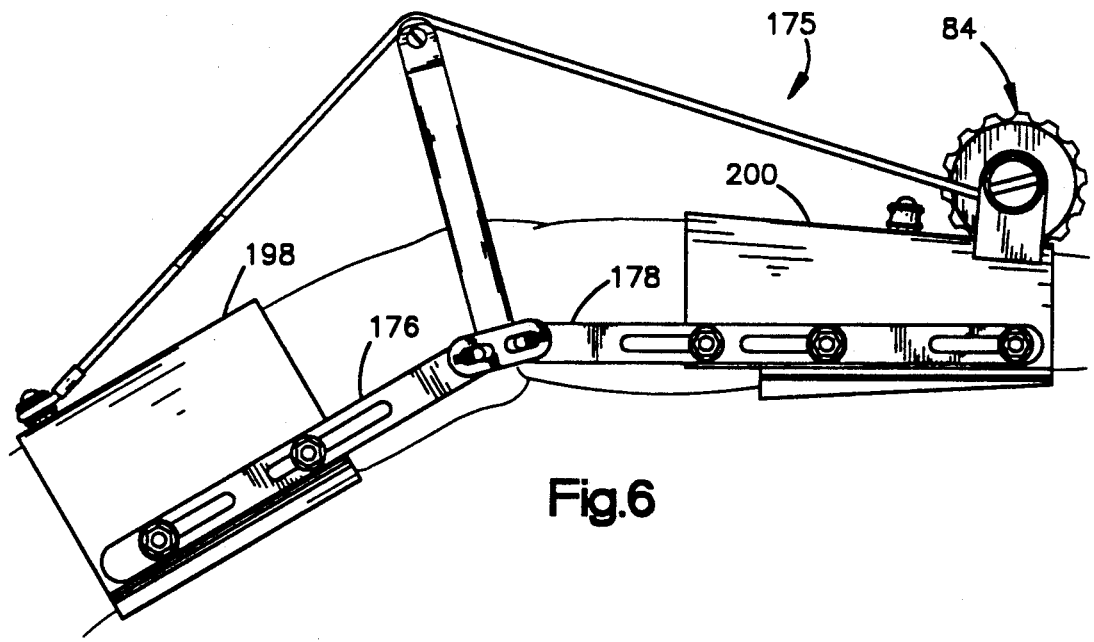
FIG. 6 is a view of an orthosis having asymmetric arm ends to effect joint distraction upon extension.

The orthosis 175 of FIGS. 6 and 7 uses as somewhat different arrangement for providing distraction force to the orthosis arms 176 and 178. Again, the inner ends of the arms 176 and 178 are geared to each other. A set of gear teeth 180 on the inner end of the arm 176 mesh with a set of gear teeth 182 on the inner end of the arm 178. The respective gear teeth are formed in a non-circular pattern on the outer edge of the arms. That is, the gear teeth 184 closer to the inner ends of the arms 176 and 178 are relatively farther from the pivot pins 186, and the gear teeth 188 are relatively closer to the cuff assemblies 190 and 192. Each arm 176 and 178 is spring-biased longitudinally inwardly by a respective spring 193 acting on a respective pivot pin 186.

Figure 7B:
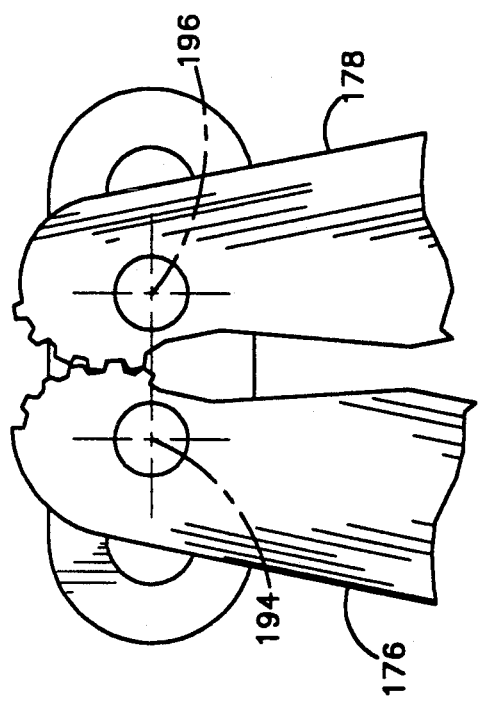
Figure 7C:
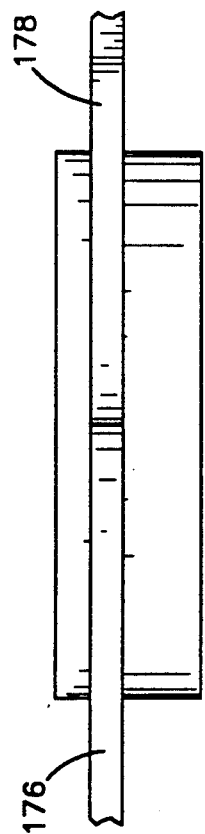
Figure 7A:
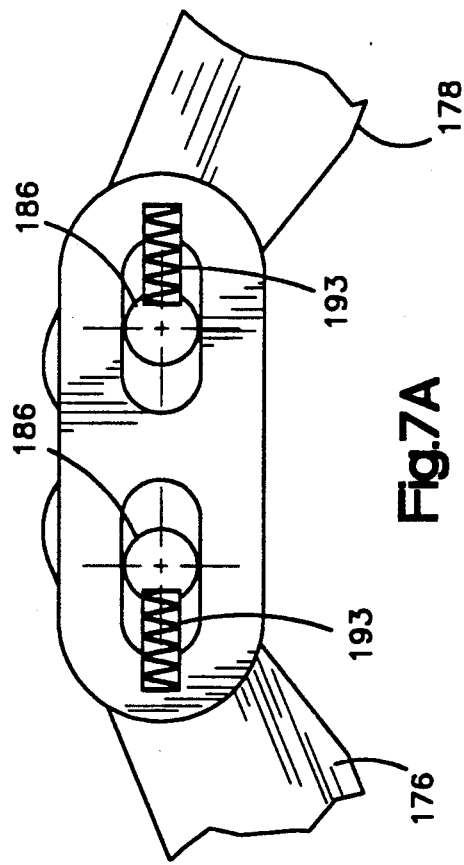

Accordingly, as the arms 176 and 178 move from a relatively flexed position as viewed in FIG. 7B to a relatively extended position as viewed in FIG. 7C, the asymmetric gear surfaces force the arms 176 and 178 longitudinally outwardly relative to each other against the bias of the springs 193. This movement is evident from a comparison of the relative locations of the pin centers 194 and 196 in FIG. 7B with their relative locations in FIG. 7C. Thus, upon rotation of the orthosis arms 176 and 178 relative to each other from a flexed position to an extended position, the orthosis arms have moved longitudinally outwardly. Because the cuffs 198 and 200 on the orthosis arms are clamped to the limb segments, the limb segments are also forced outwardly, providing joint distraction.

In accordance with the present invention, the desired distraction force can be provided by locating the axis of rotation of the brace arms outwardly from the axis of rotation of the limb. In this event, a spreading arrangement is not necessary, although it may be used.

FIGS. 8–10 illustrate schematically such a structure. An orthosis 202 includes first and second arms 204 and 206 which are relatively pivotable from a relatively flexed position as viewed in FIG. 8 to a relatively extended position as viewed in FIG. 10. The cuffs 208 and 210 on the brace arms are clamped to their respective limb segments. The center of rotation of the brace arms is represented by the point A in the outer sector A (see FIG. 1). The center of rotation of the limb joint is represented by the point B. The distance between the point A and a point C on the cuff 208 is the same as the distance between the point A and a point D on the cuff 210. The triangles in FIG. 8A illustrate the relative positions of the various points in FIG. 8.

Upon rotation of the arms 204 and 206 relative to each other from a flexed position to an extended position, the points C and D move to a relative position as shown first in FIGS. 9 and 9A then in FIGS. 10 and 10A. It can be seen clearly from FIGS. 9A and 10A that the point B has, in effect been spread apart into two points B′ and B″. This represents schematically the pulling apart of the joint of which the point B is the center of rotation. Of course, the joint is not actually pulled completely apart. Rather, the joint is distracted somewhat because the limb segments are clamped to the cuffs 208 and 210, and when the cuffs 208 and 210 move longitudinally outwardly because of the geometry of the brace, so also do the limb segments, distracting the joint to a certain amount. Distraction is limited by force-limiting means such as described above.

Furthermore, it is to be noted that a mechanical advantage is derived from having the center of rotation of the brace arms spaced apart from the center of rotation of the limb joint.

Figure 11:
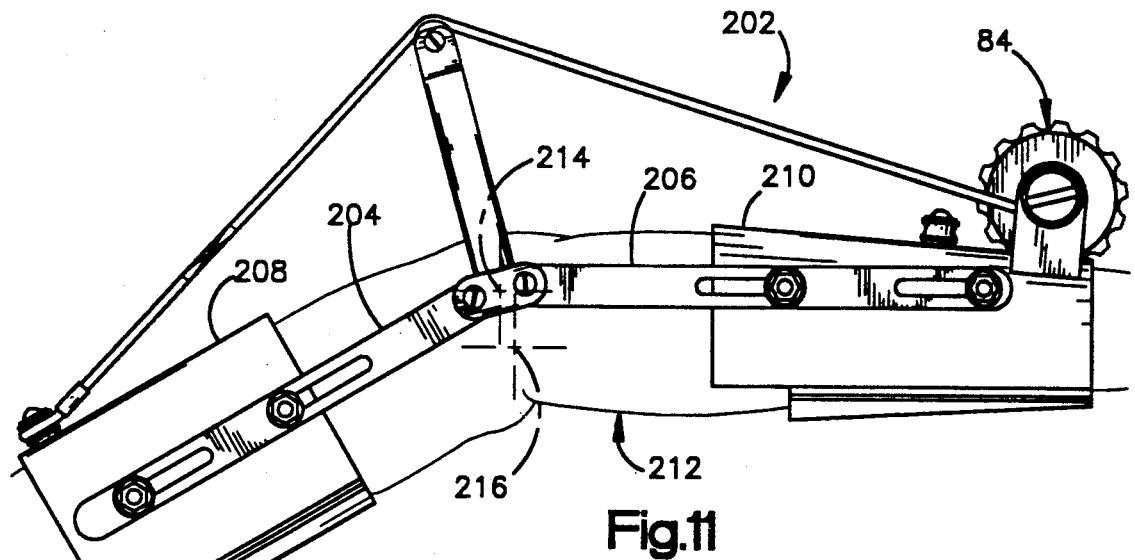
FIG. 11 is a view of an orthosis for use in extending an arm joint.

FIG. 11 shows an orthosis 202 set up to extend an elbow joint of an arm 212. The center of rotation 214 of the orthosis 202 is located outwardly of the center of rotation 216 of the limb 212 (in the outer sector B as defined with reference to FIG. 1). Upon actuation of the winch 218 to wind the flexible member 220, the orthosis arms 204 and 206 pivot from a relatively flexed position to a relatively extended position. The limb 212 is extended. Because the center of rotation 214 of the orthosis 202 is located outwardly of the center of rotation 216 of the limb 212, the elbow joint is distracted, limiting compressive forces on the tissues in the joint.

Figure 12:
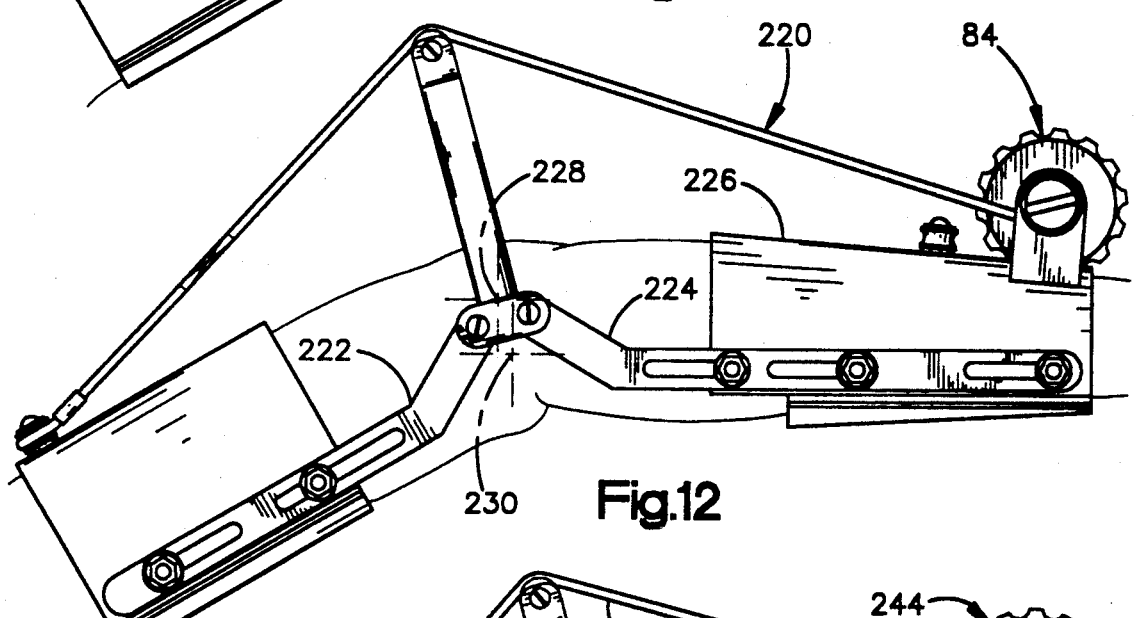
FIG. 12 is a view of an orthosis similar to the orthosis of FIG. 11 but having bent arms.

FIG. 12 shows an orthosis 220 similar to the orthosis 202 but having bent orthosis arms 222 and 224. Each arm 222 and 224 attaches to a respective cuff assembly 226 at a location farther to the inside of the limb segment. Still, the center of rotation 228 of the orthosis 220 is located outwardly of the center of rotation 230 of the limb 212. Therefore, upon extension of the orthosis 220 and the limb 212, the elbow joint is distracted, limiting compressive forces on the tissues in the joint.

Figure 13:
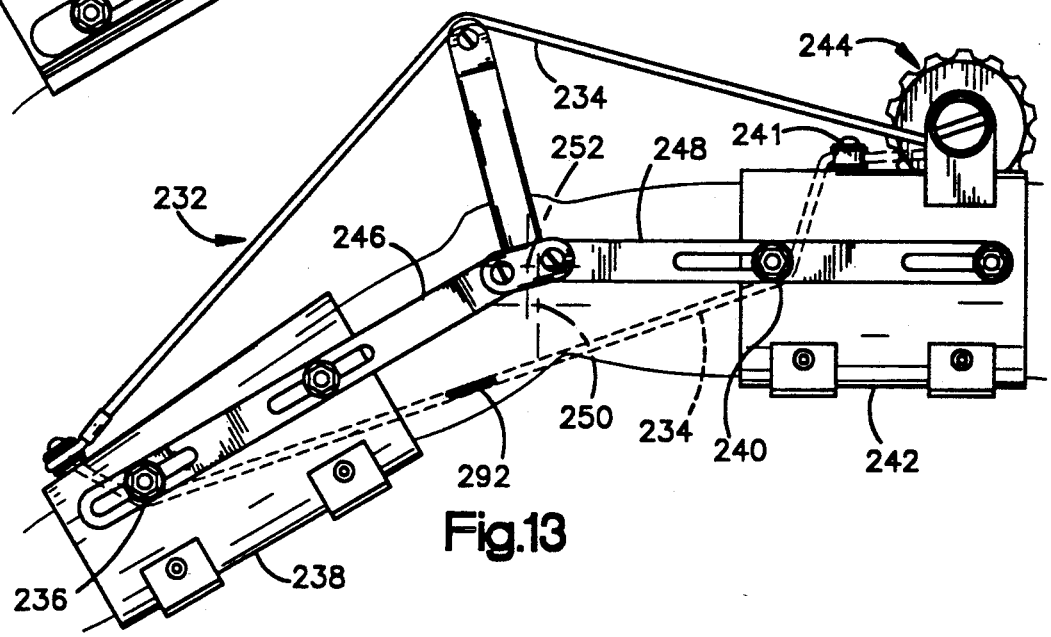
FIG. 13 is a view of an orthosis for use in extending a knee joint.

FIG. 13 shows an orthosis 232 similar to that of FIG. 11 but specifically designed to extend and flex a knee joint rather than an elbow joint. The orthosis 232 is shown in solid lines in FIG. 13 as set up for extension, while the dashed lines indicate the routing of the flexible member 234 to obtain flexion. In the flexion configuration, the flexible member 234 is routed around a pulley 236 on one cuff assembly 238, and around a pair of pulleys 240 and 241 on the other cuff assembly 242. Actuation of the winch 244 to wind the flexible member 234 causes the orthosis arms 246 and 248 to pivot relative to each other to flex the joint 250, rather than extend it. As set up for extension as shown in solid lines, the orthosis 232 distracts the joint 250 because the center of rotation 252 of the orthosis 232 is located outwardly of the joint 250.

Further, it is noted that a mechanical advantage is derived from the orthosis drive mechanism including a cable and pulley system.

The arms of the various orthoses illustrated are rigid members made of, for example, aluminum or stainless steel so as to be able to transmit the necessary forces. It should be understood that any material of sufficient rigidity can be used, including a polymeric or composite material.

It should also be noted that the flexible member 110 (FIG. 1) can include or can be replaced by a resilient member, such as an elastic member or a spring loaded member. This provides the patient with some ability to bend or flex the joint either alone or while the orthosis is attempting to extend the joint. In effect, the patient's muscles work against the force of the orthosis and provide exercise for the muscles. For example, one of the illustrated orthoses can be set up for flexion, and the patient would then attempt to extend the joint. This would provide exercise to the joint and would also provide for distraction upon joint extension, rather than compression as is common with exercise apparatus. The necessary modifications to the structures shown in the drawings are indicated by the flexible member portion 292 in FIG. 13 which is a length of the flexible member 234 which is to some extent stretchable or elastic as opposed to the remainder thereof which firmly transmits force. The portion 292 is also representative of the weakened or frangible flexible member portion used as a distraction force-limiting means.

It is apparent that the orthosis of the present invention can apply much greater forces, safely through any range of motion, as compared to a spring-driven orthosis such as in the prior art. It is further apparent that the orthosis of the present invention is operative to safely distract a joint through the joint's entire range of extension.

Further, it can be seen that the orthosis of the present invention is usable with the patient in an upright position as opposed to lying in bed, and is thus more comfortable. The orthosis is light weight and portable, because of the mechanical advantage provided by the drive mechanism. The orthosis can, when properly dimensioned, be used on any joint. It can also be used for motion other than flexion and extension, such as rotation, pronation, supination, etc., when suitably modified while incorporating the same operating principles.

Any of the orthoses of the present invention may also include means for providing three distinct areas of application of force to the limb. In addition to the two cuff assemblies which apply force at locations as far distant as possible from the joint to increase mechanical advantage, means can be provided for applying force in the opposite direction to the area of the limb adjacent the joint. This would include, for example, a cup on the outside of the elbow or knee or straps extending around the elbow or knee. Such modification can easily be made in accordance with the teachings of the prior art, and may aid in providing the desired extension force, flexion force, and/or distraction force.

From the above description of the invention, those skilled in the art will perceive improvements, changes and modifications in the invention. Such improvements, changes and modifications within the skill of the art are intended to be covered by the appended claims.

I claim:

1. An apparatus for establishing extremes of motion of a joint between first and second relatively pivotable body portions, by stretching tissue around the joint during movement of the joint, the joint and the first and second body portions defining on one side of the joint an inner sector which decreases in angle as the joint is flexed and defining on the opposite side of the joint an outer sector which decreases in angle as the joint is extended, comprising:

a first arm having proximal and distal end portions, and first clamping means on said first arm for clamping said first arm to the first body portion;

a second arm having proximal and distal end portions, and second clamping means on said second arm for clamping said second arm to the second body portion;

pivot means for pivotally interconnecting said proximal end portions of said first and second arms, at least one of said first and second arms having portions cooperating with said pivot means for forcing said proximal end portions of said first and second arms longitudinally apart from each other upon pivoting movement of said first and second arms from a relatively flexed position to a relatively extended position, to thereby exert a force upon at least one of said first and second body portions to distract the joint; and actuator means connected to said first and second arms for applying force to said first and second arms to pivot said first and second arms relative to each other to move the joint.

2. An apparatus as defined in claim 1 wherein said means operable to spread said first and second arms comprises:

means defining a cam slot in said means for pivotally connecting said first and second arms, and a pin on one of said first and second arms and received in said cam slot, said cam slot having surface means for moving said pin and thereby said one arm longitudinally outwardly relative to said means for pivotally connecting said first and second arms upon relative extension of said arms.

3. An apparatus as defined in claim 1 wherein said means operable to spread said first and second arms comprises an eccentric surface located on one of said first and second arms and in abutting engagement with the other of said first and second arms, pivoting movement of said first and second arms from a relatively flexed position to a relatively extended position causing relative movement of said abutting surfaces to move said first and second arms longitudinally outwardly relative each other.

4. An apparatus as defined in claim 1 including flexible force transmitting means connected with at least one of said arms, and drive means connected with said flexible force transmitting means for applying force to said flexible force transmitting means to move said first and second arms relative to each other.

5. An apparatus as defined in claim 4 including a rigid support member having an inner end connected with said means for pivotally connecting said first and second arms and an outer end located in the outer sector, said flexible force transmitting means being connected between a location on said rigid support member in said outer sector and said first and second arms.

6. An apparatus as defined in claim 1 wherein said pivot axis of said arms is located in the outer sector to effect distraction of the joint upon pivoting movement of said first and second arms from a relatively flexed position to a relatively extended position.

7. An apparatus as defined in claim 6 including flexible force transmitting means connected with at least one of said arms, and drive means for applying force to said flexible force transmitting means to move said first and second arms relative to each other.

8. An apparatus as defined in claim 7 including a rigid support member having an inner end connected with said means for pivotally connecting said first and second arms and an outer end located in the outer sector, said flexible force transmitting means being connected between said outer end of said rigid support member and said first and second arms.

9. An apparatus as defined in claim 1 including means for limiting the amount of joint distraction while still permitting said first and second arms to pivot relative to each other from a relatively flexed position to a relatively extended position.

10. An apparatus as defined in claim 9 wherein said means for limiting the amount of joint distraction comprises means for resiliently slidably interconnecting said first and second clamping means to said first and second arms.

11. An apparatus as defined in claim 9 wherein said actuator means comprises rotatable drive means and said means for limiting the amount of joint distraction comprises a slip clutch operatively connected with said rotatable drive means.

12. An apparatus as defined in claim 9 including flexible force transmitting means connected with at least one of said arms, and wherein said means for limiting the amount of joint distraction comprises an elastic portion in said flexible force transmitting means.

13. An apparatus as defined in claim 9 including flexible force transmitting means connected with at least one of said arms, and wherein said means for limiting the amount of joint distraction comprises a frangible portion in said flexible force transmitting means.

14. An apparatus as defined in claim 1 wherein said actuator means comprises drive means mounted on one of said first and second arms.

15. An apparatus for establishing extremes of motion by stretching tissue around a joint between first and second relatively pivotable body portions, the joint and the first and second body portions defining on one side of the joint an inner sector which decreases in angle as the joint is flexed and defining on the opposite side of the joint an outer sector which decreases in angle as the joint is extended, comprising:
a first arm, and first clamping means on said first arm for clamping said first arm to the first body portion;
a second arm, and second clamping means on said second arm for clamping said second arm to the second body portion;
means for pivotally connecting said first and second arms with each other at a pivot axis intermediate said first and second clamping means; and
actuator means connected to said first and second arms for applying force to said first and second arms to pivot said first and second arms relative to each other to move the joint;
said first and second clamping means exerting a force upon at least one of said first and second body portions in a direction outwardly along said at least one body portion and away from said means for pivotally connecting said first and second arms with each other to distract the joint upon pivoting movement of said first and second arms from a relatively flexed position to a relatively extended position;
wherein said actuator means comprises winch means rotatable in winding and unwinding directions for winding and unwinding a cable connected with said arms and ratchet means for selectively blocking rotating movement of said winch means in a selected direction, said winch means and said ratchet means being selectively operable to provide incremental winding of said cable between a plurality of locking positions.

16. An apparatus for establishing extremes of motion by stretching tissue around a joint between first and second relatively pivotable body portions, the joint and the first and second body portions defining on one side of the joint an inner sector which decreases in angle as the joint is flexed and defining on the opposite side of the joint an outer sector which decreases in angle as the joint is extended, comprising:
a first arm, and first clamping means on said first arm for clamping said first arm to the first body portion;
a second arm, and second clamping means on said second arm for clamping said second arm to the second body portion;
means for pivotally connecting said first and second arms with each other at a pivot axis intermediate said first and second clamping means; and
actuator means connected to said first and second arms for applying force to said first and second arms to pivot said first and second arms relative to each other to move the joint;
said first and second clamping means exerting a force upon at least one of said first and second body portions in a direction outwardly along said at least one body portion and away from said means for pivotally connecting said first and second arms with each other to distract the joint upon pivoting movement of said first and second arms from a relatively flexed position to a relatively extended position;
said actuator means comprising drive means mounted on one of said first and second arms, said drive means comprising winch means rotatable in winding and unwinding directions for winding and unwinding said cable and ratchet means for selectively blocking rotating movement of said winch means in a selected direction, said winch means and said ratchet means being selectively operable to provide incremental winding of said cable between a plurality of locking positions.

17. A orthosis for stretching tissue around a joint between first and second relatively pivotable body portions, the joint and the first and second body portions defining on one side of the joint an inner sector which decreases in angle as the joint is flexed and defining on the opposite side of the joint an outer sector which decreases in angle as the joint is extended, comprising:
a first arm, and first clamping means on said first arm for clamping said first arm to the first body portion;
a second arm, and second clamping means on said second arm for clamping said second arm to the second body portion;
means for pivotally connecting said first and second arms with each other at a pivot axis intermediate said first and second clamping means; and
actuator means connected to said first and second arms for receiving force not generated by relative pivotal movement of said first and second body portions and for applying force to said first and second arms to pivot said first and second arms relative to each other to move the joint;
wherein said pivot axis of said arms is spaced apart from the axis of rotation of the joint and disposed in the outer sector to effect distraction of the joint upon pivoting movement of said first and second arms from a relatively flexed position to a relatively extended position.

18. An orthosis as set forth in claim 17 including flexible force transmitting means, drive means connected with said flexible force transmitting means for applying force to said flexible force transmitting means at a location in the outer sector to move said first and second arms relative to each other to move the joint.

19. An orthosis as set forth in claim 18 including a rigid support member having an inner end connected with said means for pivotally connecting said first and second arms and an outer end located in the outer sector, said flexible force transmitting means being connected between said outer end of said rigid support member and said first and second arms.

20. An apparatus as defined in claim 17 wherein said pivot axis of said arms is located in the outer sector.

21. An orthosis as set forth in claim 17 wherein said actuator means comprises a tower projecting into said outer sector from said means for pivotally connecting said first and second arms with each other and a manually engageable member on said tower for receiving the force to pivot said first and second arms relative to each other to move the joint.

22. An orthosis as set forth in claim 17 wherein said actuator means for receiving force not generated by relative pivotal movement of said first and second body portions comprises a manually engageable member actuable by a patient or a therapist to apply force to said first and second arms to pivot said first and second arms relative to each other to move the joint.

23. An orthosis as set forth in claim 17 wherein said actuator means comprises a tower projecting from said means for pivotally connecting said first and second arms with each other, said tower having at least two force transmitting members extending at an angle from said tower to said arms to apply force to said first and second arms to pivot said first and second arms relative to each other to move the joint.

24. An orthosis as set forth in claim 17 wherein said first clamping means comprises a first cuff slidably mounted on said first arm and said second clamping means comprises a second cuff slidably mounted on said second arm.

25. An orthosis as set forth in claim 17 wherein said pivot axis of said arms is disposed at a location in the outer sector spaced outwardly away from said pivot axis approximately along a line bisecting the angle between said arms.

26. An orthosis for establishing terminal extremes of motion by stretching soft tissue around a joint which is located between first and second relatively movable body portions, comprising:
first and second cuff arms for connecting said orthosis to the first and second body portions; and
means for moving said first cuff arm relative to said second cuff arm about an axis intermediate said first and second cuffs, comprising drive means for receiving force applied to said orthosis and for transmitting the applied force to said first and second cuff arms to thereby move said first cuff arm relative to said second cuff arm, said drive means including means for providing a mechanical advantage by transmitting an increased force to said first and second cuff arms, comprising tower means for spacing said axis of movement of said arms apart from a force application point of said orthosis.

27. An orthosis as defined in claim 26 wherein said means for providing a mechanical advantage comprises means for spacing said axis of movement of said arms apart from the axis of rotation of the joint.

28. An orthosis for establishing terminal extremes of motion by stretching soft tissue around a joint which is located between first and second relatively movable body portions, comprising:
first and second cuff arms for connecting said orthosis to the first and second body portions; and
means for moving said first cuff arm relative to said second cuff arm about an axis intermediate said first and second cuffs, comprising drive means for receiving force applied to said orthosis and for transmitting the applied force to said first and second cuff arms to thereby move said first cuff arm relative to said second cuff arm, said drive means including means for providing a mechanical advantage by transmitting an increased force to said first and second cuff arms, comprising a cable and pulley system.

29. An orthosis for stretching tissue around a joint between first and second relatively pivotable body portions, comprising:
an elongate first cuff arm having proximal and distal end portions;
an elongate second cuff arm having proximal and distal end portions and movably connected to said first cuff arm;
a first cuff on said first cuff arm for connecting said first cuff arm to the first body portion;
a second cuff on said second cuff arm for connecting said second cuff arm to the second body portion; and
said first and second cuff arms having portions cooperating to force said proximal end portions of said first and second arms longitudinally apart from each other upon pivoting movement of said first and second arms from a relatively flexed position to a relatively extended position, to thereby exert a force upon at least one of said first and second body portions to distract the joint; and actuator means for moving said first cuff arm relative to said second cuff arm, said actuator means being selectively operable to provide incremental movement of said first cuff arm relative to said second cuff arm between a plurality of positions and to lock said arms at said positions.

30. An orthosis as defined in claim 29 wherein said means for moving said first cuff arm relative to said second cuff arm comprises ratchet drive means operable to provide incremental movement of said first cuff arm relative to said second cuff arm between a plurality of positions and to lock said arms at said positions.

* * * * *